United States Patent
Niewiadomski

(10) Patent No.: US 10,149,746 B2
(45) Date of Patent: Dec. 11, 2018

(54) METHOD OF MANUFACTURING A MOLDED DENTAL COMPONENT FROM A BLANK

(71) Applicant: DENTSPLY SIRONA Inc., York, PA (US)

(72) Inventor: Klaus Niewiadomski, Lorsch (DE)

(73) Assignee: DENTSPLY SIRONA Inc., York, PA (US)

(*) Notice: Subject to any disclaimer, the term of this patent is extended or adjusted under 35 U.S.C. 154(b) by 0 days.

(21) Appl. No.: 14/853,880

(22) Filed: Sep. 14, 2015

(65) Prior Publication Data

US 2016/0067017 A1    Mar. 10, 2016

Related U.S. Application Data

(62) Division of application No. 12/671,390, filed as application No. PCT/EP2008/060043 on Jul. 31, 2008, now Pat. No. 9,155,598.

(30) Foreign Application Priority Data

Jul. 31, 2007  (DE) .................. 10 2007 036 279
Mar. 12, 2008  (DE) .................. 10 2008 013 829

(51) Int. Cl.
*A61C 13/00* (2006.01)
*G05B 19/401* (2006.01)
*G06K 19/06* (2006.01)

(52) U.S. Cl.
CPC ...... *A61C 13/0022* (2013.01); *A61C 13/0009* (2013.01); *G05B 19/401* (2013.01); *G06K 19/06046* (2013.01); *Y10T 29/49567* (2015.01); *Y10T 29/49568* (2015.01)

(58) Field of Classification Search
CPC ............ A61C 13/0022; A61C 13/0009; A61C 13/0004; G06K 19/06046; G06K 19/06009; Y10T 29/49567; Y10T 29/49568

See application file for complete search history.

(56) References Cited

U.S. PATENT DOCUMENTS 3,665,493 A * 5/1972 Glowzewski ...... G05B 19/4163
                                                                318/561
4,615,678 A * 10/1986 Moermann ............. A61C 5/10
                                                                428/542.8
6,311,100 B1* 10/2001 Sarma ................ G05B 19/4097
                                                                700/186

(Continued)

FOREIGN PATENT DOCUMENTS

DE   102005041693 A1 *  3/2007  ......... A61C 13/0022
WO   WO1999013796 A1 *  3/1999

(Continued)

*Primary Examiner* — Sarang Afzali
*Assistant Examiner* — Ruth G Hidalgo-Hernandez
(74) *Attorney, Agent, or Firm* — Dentsply Sirona Inc.

(57) ABSTRACT

A method for producing a dental shaped body from a blank that has a corpus of tooth restoration material by a tool adapted to remove the material. To detect a position of the corpus inserted in a machining device, contact scanning is performed on the blank by the tool. At least one dimension of the blank corpus is detected, and the machining tool is prepositioned for a contacting operation according to the detected at least one dimension of the blank corpus.

14 Claims, 7 Drawing Sheets

(56) References Cited

U.S. PATENT DOCUMENTS

| | | | | |
|---|---|---|---|---|
| 6,394,880 B1* | 5/2002 | Basler | A61C 13/0022 | 451/28 |
| 6,485,305 B1* | 11/2002 | Pfeiffer | A61C 5/10 | 428/542.8 |
| 6,640,150 B1* | 10/2003 | Persson | A61C 13/0003 | 409/96 |
| 7,178,731 B2* | 2/2007 | Basler | A61C 13/0022 | 235/454 |
| 7,985,119 B2* | 7/2011 | Basler | A61C 13/0003 | 433/202.1 |
| 8,057,912 B2* | 11/2011 | Basler | A61C 13/0003 | 428/542.8 |
| 8,401,690 B2* | 3/2013 | Gleditzsch | A61C 13/0004 | 433/201.1 |
| 8,443,502 B2* | 5/2013 | Galehr | A61C 13/0022 | 29/281.1 |
| 8,673,454 B2* | 3/2014 | Basler | A61C 13/0003 | 428/542.8 |
| 9,155,598 B2* | 10/2015 | Niewiadomski | A61C 13/0009 | |
| 2002/0076530 A1* | 6/2002 | MacDougald | A61C 13/0003 | 428/195.1 |
| 2003/0073394 A1* | 4/2003 | Reidt | A61C 13/0022 | 451/398 |
| 2005/0008989 A1* | 1/2005 | Rothenberger | A61C 13/0022 | 433/202.1 |
| 2005/0254064 A1* | 11/2005 | Basler | A61C 13/0022 | 356/601 |
| 2006/0141250 A1* | 6/2006 | Basler | A61C 13/0003 | 428/364 |
| 2006/0292527 A1* | 12/2006 | Basler | A61C 13/0003 | 433/213 |
| 2010/0297580 A1* | 11/2010 | Niewiadomski | A61C 13/0009 | 433/167 |
| 2011/0229857 A1* | 9/2011 | Niewiadomski | A61C 13/0009 | 433/201.1 |

FOREIGN PATENT DOCUMENTS

| | | | | |
|---|---|---|---|---|
| WO | WO 0132093 A1 * | 5/2001 | | A61C 13/0003 |
| WO | WO 2007025997 A1 * | 3/2007 | | A61C 13/0022 |
| WO | WO 2008128946 A1 * | 10/2008 | | A61C 13/0004 |

* cited by examiner

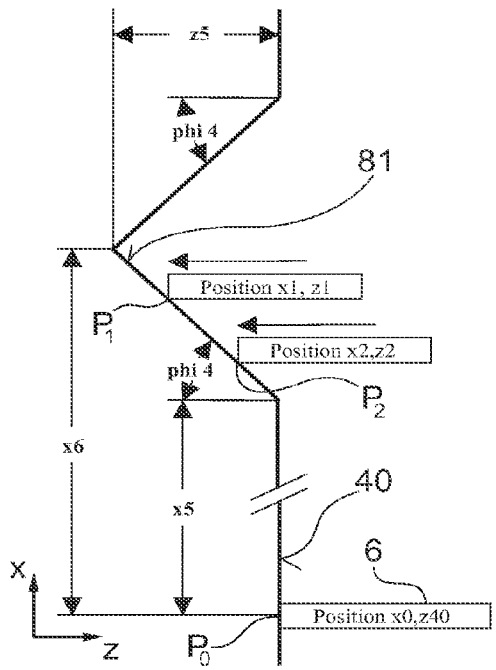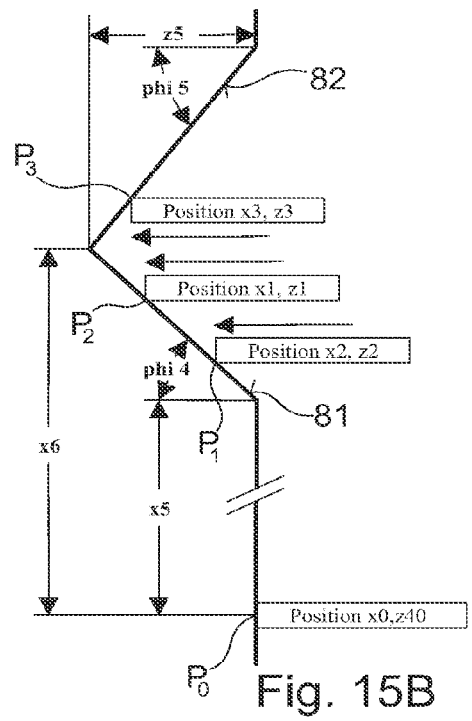
Fig. 15A  Fig. 15B
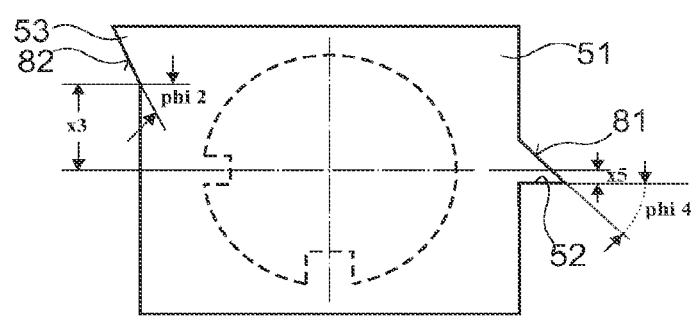
Fig. 16A
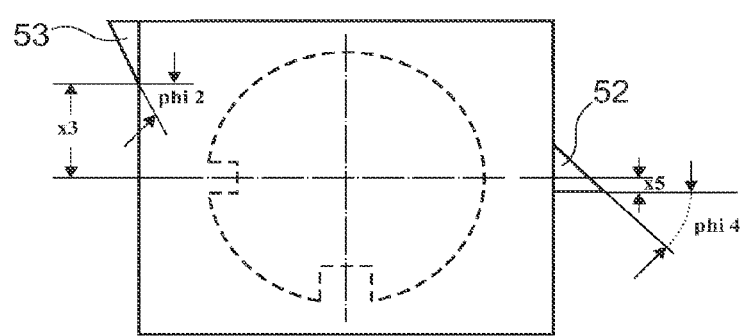
Fig. 16B

METHOD OF MANUFACTURING A MOLDED DENTAL COMPONENT FROM A BLANK

CROSS REFERENCE TO RELATED APPLICATIONS

The present application is a divisional of U.S. Pat. No. 9,155.598, which entered the national stage on Jun. 22, 2010, which claims priority to the U.S. National Stage Entry of international Patent Application No. PCT/EP2008/060043, filed Jul. 31, 2008, which claims priority to German Patent Application Nos. 102007036279 and 102008013829, filed Jul. 31, 2007, and Mar. 12, 2008, respectively. The entire disclosure of each such prior application is incorporated by reference in its entirety, as if set forth fully herein.

BACKGROUND OF THE INVENTION

The invention relates to a blank for the production of dental shaped bodies, the blank comprising a corpus of dental restoration material, from which the shaped body can be carved with the aid of a tool adapted to cause removal of material, the blank comprising a coding means incorporating at least one structure as an information carrier for characteristics of the blank corpus, the position, dimensions, or nature of the structure being detectable by scanning or measuring the blank. The invention further relates to a method of producing a dental shaped body from a blank comprising a corpus of dental restoration material with the aid of a tool adapted to cause removal of material, provision being made for a contacting operation of the tool on the blank corpus for detecting the position of the blank corpus.

In order to carve a dental shaped body from a blank by the removal of material, the shaped body to be carved must be entirely enclosed within the corpus of the blank. For optimization of the machining process, it is advantageous when the blank is one selected from a plurality of blanks having corpuses of various sizes, since the volume of the blank corpus to be made available can then be one suitable for the shaped body to be produced. Since every blank corpus is larger than the shaped body, it is advantageous to orient the shaped body within the blank corpus in such a way that the machining process can be optimized. For example, a shaped body can be placed in an oblong blank at the outer end of the blank corpus in order to reduce the volume of material to be removed.

PRIOR ART

It is known from the prior art to measure the corpus of the blank inserted into the machining device, for example, by means of optical scanning using a rangefinder or by moving the machining tools toward the blank corpus, which procedure is referred to as contact scanning. When measuring with the aid of a contacting operation, however, it is necessary that the tool be slowly advanced toward the blank corpus starting from the largest possible contour of the blank corpus. Particularly in the case of small blank corpuses, there can be large distances between the starting position of the contacting operation and the actual surface of the blank corpus. These long contact-demanding distances result in a correspondingly long contacting period. Since a rotational speed control takes place during the entire contacting period in order to determine when the machining tool makes contact with the surface of the blank corpus, errors indicating a premature contact can arise in the rotational speed control means during a long contacting operation without the tool having actually touched the surface of the blank corpus.

EP 0 160 797 discloses a blank for the production of dental shaped bodies, which blank is composed of a handle and corpus of different materials. A reference surface on the handle can be formed in such a way that control information for the machining process reflecting the characteristics of the blank can be deduced. For this purpose, the reference surface is formed such that regions in the form of binary coding means distributed over the circumference of the handle either correspond to the circumferential surface or are flattened.

The position of the abrasion-prone tools used for machining the blank is adjusted in that the tools are moved to engage defined reference surfaces of the blank. These reference surfaces can be on the handle, as shown in EP 0 160 797, or as shown in DE 196 12 699, they can be positioned on the blank corpus or on its own reference part located on the blank at more or less arbitrary places.

A blank is disclosed in DE 103 30 758 A1, which blank exhibits at least one gage that is geometrically formed in such a way that the tool selected for machining can be identified from its outer contour by means of the gage. A contacting operation is used for this purpose.

In DE 10 2004 063 417 A1, the blank is formed such that at least two gages are provided, each of which is in the form of a recess, the geometry of the recesses being such that the tool selected for machining can be identified from its outer contour by means of the at least one gage, the at least two gages being located on the blank such that they can be simultaneously engaged by the at least two tools when the blank is clamped in the machining device for machining thereof. Here again, a contacting operation is used.

A solution for determining the size of the blank corpus consists in specifying the size of the blank corpus to the machining device irrespective of the actual size of the blank inserted in the machining device. The selection can be made, for example, by means of a selection dialog on the machining device itself or with the aid of a software program for controlling the machining device via a PC. The use of a blank other than that specified to the machining device can result in the blank corpus shearing off from a handle, or in the tools being spoiled or serious damage occurring to the machining device itself.

Hitherto, the user has thus himself had to be responsible for ensuring that the blank inserted in the machining device conforms to the selected blank with respect to manufacturer, material, type, and size. The user has also been responsible for ensuring that no material other than that permissible for the tools employed be used.

However, it is known from the prior art that the shrinkage factors required for some materials are incorporated in the system by means of a scanner built into the machining device and forming an alternative to manual input.

For optimum control of the machining device, it is advantageous to obtain both knowledge of the material to be machined and the type and size of the blank used. For example, a cylindrical or cuboid blank corpus composed of different materials can be used. As a result of the plurality of the materials, not every material can be machined by all of the tools present so that knowledge of the material characteristics is in fact indispensable.

Specifying the characteristics of the blank to the machining device irrespective of the blank actually inserted in the machining device, can lead to fitting inaccuracies of the shaped body or to premature destruction of the tools due to errors or to bypassing recommendations. Furthermore, minimum wall thicknesses must be observed, depending on the restoration material, so that if the material used does not conform to the one selected, this can result in a defective shaped body having extremely low strength characteristics. Excessively small wall thicknesses can also lead to breakage of the partially produced shaped body before the machining operation in the machining device has terminated.

It is an object of the present invention to reduce the long contacting times and the accompanying prolongation of the machining time and to carry out user-independent control of the correct selection of the blank inserted in the machining device at least with respect to the dimensions thereof.

SUMMARY OF THE INVENTION

The blank of the invention for the production of dental shaped bodies comprises a corpus of dental restoration material, from which the shaped body to be produced can be carved with the aid of a tool adapted to cause removal of material. The blank comprises coding means incorporating at least one structure as a carrier of information concerning the characteristics of the blank corpus, the structure being located on the blank such that the position, dimensions, or nature of the structure can be detected by scanning or measuring the blank. The position, dimension, or nature of the structure is such that the value acquired when detecting it corresponds to analog information concerning a characteristic of the blank corpus.

The analog information can correspond to a fraction of a characteristic of the blank to be described in analog form, and can be derived from or directly given by, in particular, the amount of deviation of the structure from a predefined reference surface. Possible examples of such characteristics include the strength of or a multiplication factor for, the material of the blank and also information concerning the position of further structures or reference surfaces.

According to the present invention, the block-specific dimensions can be stored in the geometric design of the blank corpus or of the corpus handle itself and implemented for automatic prepositioning of the tool in a contacting operation on the blank.

Knowledge of the dimensions of the blank corpus used reliably prevents the blank corpus from shearing off, the tools from being spoiled and the machining device itself from being damaged, as could occur when an unknown blank corpus is used.

According to an advantageous development of the invention, the coding means can be in the form of a geometric structure, the dimension of which, following a predefined mathematic function, corresponds to at least one dimension of the blank corpus. For example, the depths of depressions in the blank corpus or in the radius of the corpus handle indicate an analog, true-to-scale representation of the assigned maximum dimensions of the blank corpus. Scanning the geometric design of the structures requires, due to their known positions, much shorter distances and less time than scanning an entire blank corpus of initially unknown dimensions.

The provision of analog information on the blank itself makes it unnecessary to refer to tables or databases. Thus external information concerning the information content of the measured variables need not be transferred to the machining device or stored therein.

Further information, such as material characteristics, strength, color, translucency, shrinkage factors, etc. can be additionally included in the coding means, if appropriate, provided this information can be displayed in analog form, for example in the form of a scale of from 0 to 100%.

Advantageously, an additional structure providing control information concerning a function of at least two dimensions of at least two structures can be formed. The at least two structures may be provided jointly, for example in a common geometric design in the form of a groove of defined width and depth.

Advantageously, a structure can comprise at least one surface, the deviation in the position, dimension, or nature of surface from a predefined reference surface being representative of an analog information concerning the blank corpus. A plurality of structures can interact and form, for example, a groove.

The predefined reference surface can be the circumferential surface of the handle or, in the case of structures located on the blank corpus, a lateral surface or end surface of the blank corpus.

The structure can be positioned around a longitudinal axis of the blank, for example, on a circumferential surface of the handle or on a lateral surface of the blank corpus.

Advantageously, the location of the structure is independent of the longitudinal axis of the blank and is related to a manufacturing center axis. During the production of the structure, a machining process takes place, and this machining process results in the presence of a manufacturing center axis. Decoupling the manufacturing center axis of the structure from the longitudinal axis of the blank facilitates production.

Advantageously, at least one reference surface is provided for establishing the position of the manufacturing center axis.

For the purpose of detecting the position of the structure relative to the reference position, a reference structure having a reference position may be provided. The position of the structure is thus independent of the remaining geometry of the blank.

Advantageously, the degree of deviation from the reference position can comply with information concerning at least one geometric dimension of the blank corpus.

According to a development of the invention, the reference surface of the structure can be disposed in a depression formed toward the longitudinal axis of the blank, and is preferably at the base of a groove.

Advantageously, a reference surface can be provided on the blank for determining the eccentricity of the structures carrying information relative to a rotation axis of the blank accommodated in a machining device for machining purposes. The correlation between the reference surface and the structure is in this case known.

Advantageously, the groove width and/or the groove length can provide information concerning the characteristics of the blank corpus.

According to an advantageous development of the invention, the blank can include a handle for the corpus, and the structure can be located on this handle. This makes it possible to produce the handle and blank corpus independently of each other, while the blank corpus need not have high-precision geometries. The structures can also be located partly on the handle and partly on the blank corpus or even all on the blank corpus. Advantageously, the structure is hidden relatively to the blank corpus. This may be achieved by providing a partition plate between the handle and the blank corpus.

According to a development of the invention, the structure is located on a part that has been injection-molded onto the blank corpus or the handle.

It can be advantageous when the structure is on a separately produced part disposed between the handle and the blank corpus or on the handle itself. The separate part can be an injection-molded part or a punched part, etc., which is attached to the blank, the corpus handle or between the handle and the blank corpus.

According to an advantageous development of the invention, at least some of the structures can be disposed on the blank corpus, the advantage being that specific characteristics of the blank corpus are then stored on the corpus itself so that a standard handle can be used.

Furthermore, it can be advantageous when the blank comprises a handle and a corpus and that a structure revealing the position of at least one further structure is located on the blank corpus or a reference surface is provided on the handle. Using such a design of a structure on the handle, information can be acquired concerning the blank corpus and particularly concerning the position of the additional structures or reference surfaces on the blank corpus as soon as the machining tool makes contact with the handle in a known predefined position. This is advantageous when the handle is produced with high precision and provides information relevant to the blank corpus. The contacting operation on the structure or the reference surface of the blank corpus can then be carried out time-effectively.

The structure can be formed with a variable height, width, or length relative to a reference surface. Its angular position can also provide information.

A further object is a method of producing a dental shaped body from a blank comprising a corpus of dental restoration material with the aid of a tool adapted to cause removal of material, provision being made for a contacting operation of the tool on the blank for detecting the position of the blank corpus inserted in the machining device. At least one relevant dimension of the blank corpus is acquired in a first step, and the machining tool for the contacting operation is prepositioned on the blank corpus in a second step according to said detected dimension of the blank corpus.

Advantageously, delimitation for the distance traveled in the contacting operation, according to the detected size of the blank corpus is provided, particularly with output of an error message. In this way, a deviation from an expected contacting position can thus be detected which suggests an already partially machined blank, for example.

Advantageously, a change in the structure and/or the production of an additional structure can be carried out by means of the tool following a successful contacting operation and/or after machining the blank corpus. This makes it possible to include information concerning the machined condition of the blank.

A further object of the invention relates to a method of producing a dental shaped body from a blank comprising a corpus of dental restoration material with the aid of a tool causing removal of material, provision being made for a contacting operation of the tool on the blank for detecting the position of the blank corpus inserted in the machining device. At least one relevant dimension of the blank corpus is acquired in a first step. The tools required for the machining operation are determined in a second step depending on the detected dimensions of the blank corpus.

Advantageously, coding means provided on the blank and incorporating at least one geometric structure whose dimensions, corresponding to a function, reflect in analog form at least one dimension or an analog characteristic of the blank corpus, can be detected for determining the size of the blank corpus.

It is particularly advantageous when the acquired value is converted to a length specification using a conversion function independent of the blank with which the tool has made contact, which conversion function is stored in the machining device or in a control system for the machining device.

Advantageously, an additional structure is detected that represents control information concerning the consistency of information of at least two further structures. Here again, two structures may be combined in a common structure, for example in a groove revealing the groove width and groove depth.

It is particularly advantageous to have the possibility of stopping the machining operation in the case of incorrect control information. This can prevent defective production from the outset.

Advantageously, the coding means for revealing the size of the blank can be scanned by means of at least one tool in a contacting operation.

The position of the structure disposed on the blank corpus can be found by detecting a structure located on the handle or on the blank corpus.

A structure can also serve as control information by modifying it with the aid of the tools so as to form a flag indicating a partially machined blank corpus, e.g. the material hitherto removed.

The structures can be produced cost-effectively just as an already existing positioning groove for positioning the blank in a machining device.

As disclosed in the prior art, additional information can be present in the coding means, which information refers to a database for acquiring associated data relating, for example, to the manufacturer.

BRIEF DESCRIPTION OF THE DRAWINGS

An exemplary embodiment of the invention is shown in the drawings, in which.

EMBODIMENT OF THE INVENTION

Figure 1:
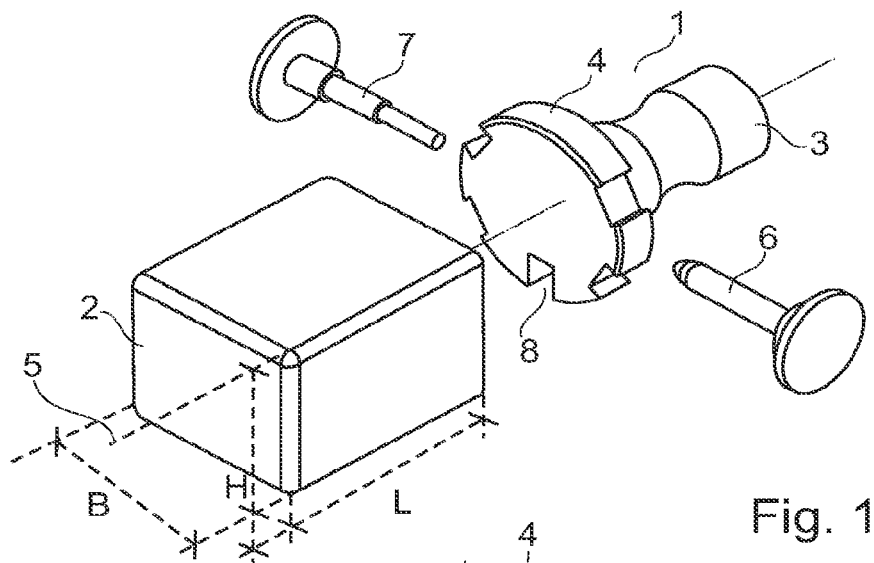
FIG. 1 shows a blank consisting of a handle and a blank corpus.

FIG. 1 shows a blank comprising a blank corpus 2 mounted on a handle 1, the blank corpus 2 being shown as detached from the handle 1 for the purpose of better illustration of the latter.

The handle 1 comprises a shank 3 and a disk 4, the shank 3 being designed for mounting the handle 1 in a machining device (not shown in the figures) and the disk 4 being designed for providing a sufficient joining area for the blank corpus 2 that is usually of a different material from that of the handle 1. However, it is possible for the handle and the blank corpus to be formed integrally.

Tools 6, 7 are disposed one on each side of the handle 1, that is, each tool is disposed to one side of a longitudinal axis 5 of the handle 1, while the tool 6 can be in the form of a cylindrical grinder having a conical tip and the tool 7 to be in the form of a cylindrical stepped grinder. The shape of the tools, however, is irrelevant to the present invention.

A groove 8 is provided in the disk 4 for positioning the handle 1, and thus the blank corpus 2 joined to the handle 1, in the machining device. In place of the groove 8 in the disk 4, a positioning aid can be disposed on the shank 3, for example a depression at one end of the handle 1, which depression cooperates with a projection in the holding device of a machining device.

Figure 2:
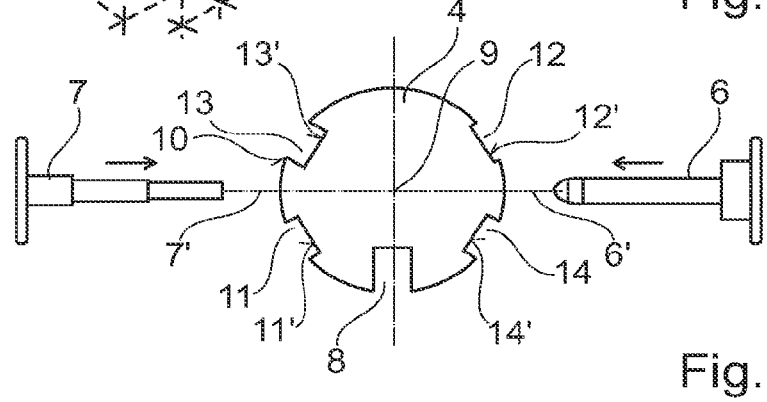
FIG. 2 is a top view of the handle shown in FIG. 1 in a reference position (positioning groove 8 below)

FIG. 2 illustrates the manner in which, starting from a known center of rotation 9 of the handle 1 clamped in a machining device (not shown), a reference position is determined for the tip of the respective tool 6, 7. This is done in that the tools 6, 7 are rotated about their longitudinal axis at low rotational speed and with low energy and advanced toward the handle in the radial direction, as viewed from the handle 1. The tools stop on coming into contact with the circumferential surface 10 of the disk 4, and the positions of the tools are registered. The positions of both grinders relative to the handle 1 are determined from the positions assumed by the tools 6, 7 upon stopping. This process is referred to as "contact scanning".

This determination of the position of the tip of the tool 6, 7 is advantageous since the tip of the tool is subject to wear that can lead to erroneous machining results on the one hand or erroneous results when sensing the handle 1. As an alternative to tool tip-sensing, i.e. contacting the handle, a contactless scanning procedure, for example an optical scan can be carried out.

In the present exemplary embodiment, the diameter of the disk 4 is manufactured with high precision, i.e. at a tolerance of 10 μm.

In addition to the relatively accurate dimensions of the diameter of the disk 4, the eccentricity of the disk 4 relative to a center of rotation 9 of the handle 1 clamped in the machining device, which center of rotation is specific to a machining device, is also relevant. However, the methods of determining this eccentricity are assumed to be known from the prior art for the purposes of the present invention.

It can be seen from FIG. 2 that, in addition to the groove 8, there is provided, for positioning the handle in the machining device, a coding means incorporating two pairs of opposing structures 11, 12 and 13, 14, the structures 11 to 14 being in the form of depressions in the circumferential surface 10 of the disk 4, and surfaces 11' to 14' being present in the structures 11 to 14. The structures 11 to 14 are distributed in such a way on the circumferential surface 10 of the disk over the circumference thereof that they are located outside the sphere of action of the tools 6, 7 along the axes 6', 7' in the reference position illustrated. The structures 11 to 14 are located at a predetermined angle relative to the groove 8 for positioning the handle 1 in the machining device, which angle is known to the machining device.

The coding means can be in the form of radial and/or axial structures that can be distributed over the circumference of the disk.

Figure 3:
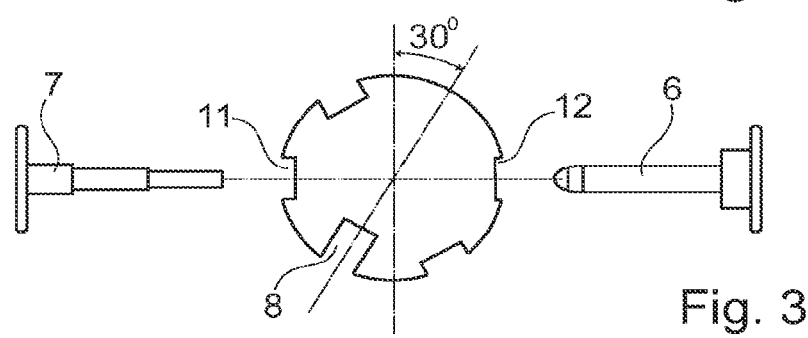
FIG. 3 shows the handle shown in FIG. 2 in a position rotated through 30° for detecting a first pair of structures.

In FIG. 3, the handle 1 shown in FIG. 2 is rotated through an angle of 30° in the clockwise direction so that the groove 8 is displaced from its central position toward the machining tool 7. In this position, the first pair of structures 11, 12 is brought into the sphere of action of the tools 7, 6 so that the tools 6, 7 come into contact with the surfaces 12', 11' of the structures 12, 11 when the tools 6, 7 are advanced.

Two analog measured values for the dimensions of the structures 11, 12 can be derived by comparing the positions of the tools 6, 7 on reaching the surfaces 12', 11' of the structures 12, 11 on the circumferential surface 10 relative to the reference position. The analog measured value determined with the aid of the tool 6 and the structure 12 can correspond, for example, to a true-to-scale length of the blank corpus 2, that is to say, multiplied by a known factor, so that the length of a function is subsequently determined from the measured value. The second measured value determined with the aid of the tool 7 and the structure 11 can represent, for example, the width of the blank corpus 2, again optionally with the use of a function involving multiplication by a known factor. The respective measured value modified by the factor can optionally be provided with a known offset within the scope of the analog function, in order to increase accuracy. In this case, the underlying function would be a linear equation having a slope corresponding to the factor and an axis intercept corresponding to the offset. The assignment of a variable to the analog measured value can alternatively be carried out by means of some other mathematical function.

A measured value can also be derived from the distance between the two structures 11, 12 of a pair. However, the disadvantage in this case is that only one measured value is obtained by means of two structures 11, 12 instead of two possible measured values.

Figure 4:
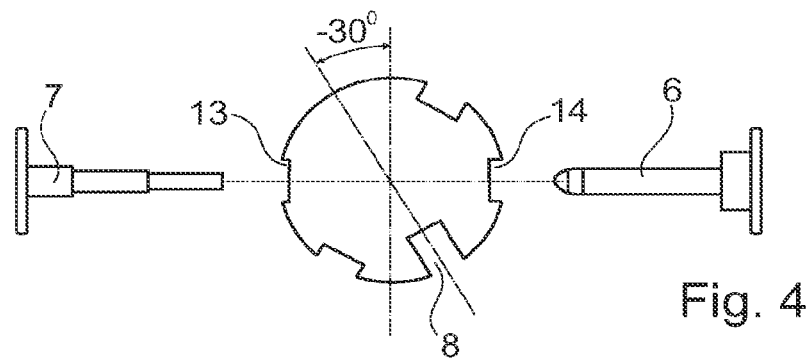
FIG. 4 shows the handle shown in FIG. 2 in a position rotated through −30° for detecting a second pair of structures.

In FIG. 4, the handle 1 shown in FIG. 2 is rotated through an angle of 30° in the anticlockwise direction about the center of rotation 9 so that the second pair of structures 13, 14 is situated in the sphere of action of the tools 6, 7. By advancing the tools 6, 7 toward the surfaces 14', 13' of the structures 14, 13, two measured values can again be derived which represent, in the form of analog values, a height h of the blank corpus 2 in the case of the structure 13, or in the case of the tool 7 and the structure 14, a measured value for a control variable for the sum of the measured values relating to height, width, and length of the structures 11, 12, and 13.

In the exemplary embodiment described above, the measured value determined with the aid of the tool contacting a structure provides analog information. For example, a length L of the blank corpus 2 of 26 mm can be assigned to a penetration depth of 1.3 mm of the structure 12. With increasing penetration depth, there is an increase in the measured value and thus of the corresponding length of the blank corpus 2. For example, in the case of a penetration depth of 1.6 mm, a length L of the blank corpus 2 of 32 mm can be deduced. The conversion factor between the measured difference of the tool tip on the circumferential surface relative to the structure 12 can be multiplied by the factor 20 in this case. For the width and height, the same or a different conversion factor, for example 10 for the height, and 15 for the width, can be implemented in the machining device. In the case of an overall measuring inaccuracy of 50 µm, the error in the converted linear dimension is at the most 1 mm, so that the error when prepositioning the tools on the blank corpus is limited to this dimension.

In this case of a blank corpus having a length L=32 mm, the control value is calculated to give a width b=12 mm and a height h=10 mm using the factors (0.8 mm+1.6 mm+1.0 mm=3.4 mm). If this value lies outside the value that can be provided by the structure, it can be divided by a factor 2 or 4, based on the correction value.

The detection of the coding means on the blank can be carried out particularly rapidly if the position of the structures is known exactly so that the tools can be brought close to the structures before the actual contacting operation begins. The loss of time as a result of these additional scanning operations is small as opposed to the gain in time in the subsequent contact scanning of the blank corpus, particularly in the case of small blocks in which the slow contacting operation proceeds from the starting position for the largest possible blank corpus.

For determining the starting position of the tool for the contacting operation on the blank corpus 2, its manufacturing tolerance for the dimensions and its orientation relative to the handle 1 must additionally be allowed for, as in the prior art.

Furthermore, the starting position for prepositioning the tool for the contacting operation can also have a preadjusted offset. The starting position of the tool is given by the distance of the tool from the rotation axis of the machining device resulting from the analog measured value of the structure multiplied by the conversion factor plus the offset. The offset can advantageously range from 1 to 5 mm and it reduces errors in the case of the larger conversion factors.

The structures 11 to 14 can also be eminences instead of the recesses illustrated. The advantage in forming the structures as recesses is that the tool can initially be advanced at high speed until it reaches the vicinity of the circumferential surface 10, and only then is it slowly brought closer to the structure.

Figure 5:
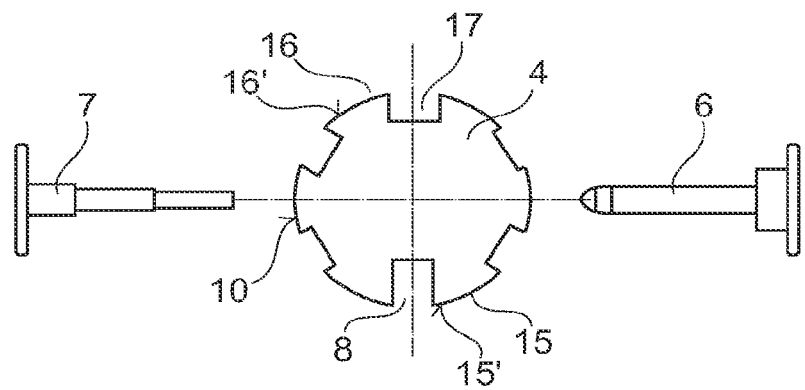
FIG. 5 shows a further handle comprising an additional pair of structures disposed at a known distance from each other.

FIG. 5 shows a further exemplary embodiment of the handle 1. On its circumferential surface 10, the disk 4 has a third pair of structures 15, 16 in addition to the two pairs of structures already described with reference to FIG. 2, which structures 15, 16 are again located opposing each other and on a part of the circumferential surface 10 that is unaffected by the groove 8 and the structures shown in FIG. 2. In the present case, the structures 15, 16 are formed such that they can provide a reference for the depth information of the other structures and are additionally spaced from each other by a distance within a close tolerance range. This tolerance range is about 10 µm. This means that the structures 15, 16 are positioned very precisely relatively to the two pairs of structures so that a type of zero position for the other structures can be derived from the structures 15, 16.

Figure 6:
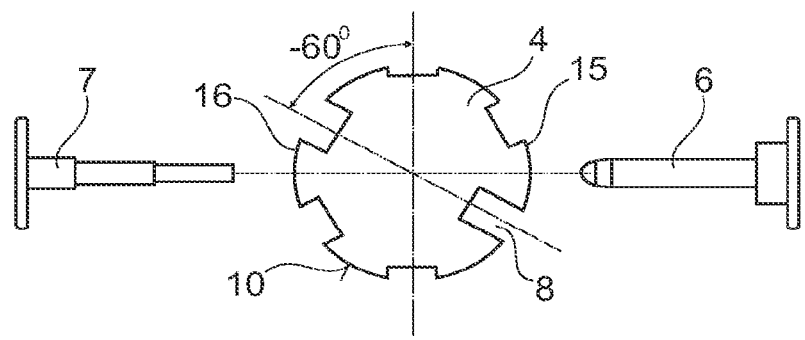
FIG. 6 illustrates a contact scanning procedure on the handle shown in FIG. 5 in the region of the additional structures.

The reference is provided for the other structures as a result of the approach of the tools 6, 7, as illustrated in FIG. 6, toward the handle 1, which has been rotated through an angle of about 60° in the anticlockwise direction, toward the structures 15, 16. A correction for the depth information of the structures 11 to 14 can be determined from the known positions at which the tips of the tools 6, 7 contacted the structures 15, 16. This is of advantage, e.g. when the position of the tool used for creating the structures is not exactly adjusted to the radius of the disk 4.

Figure 7:
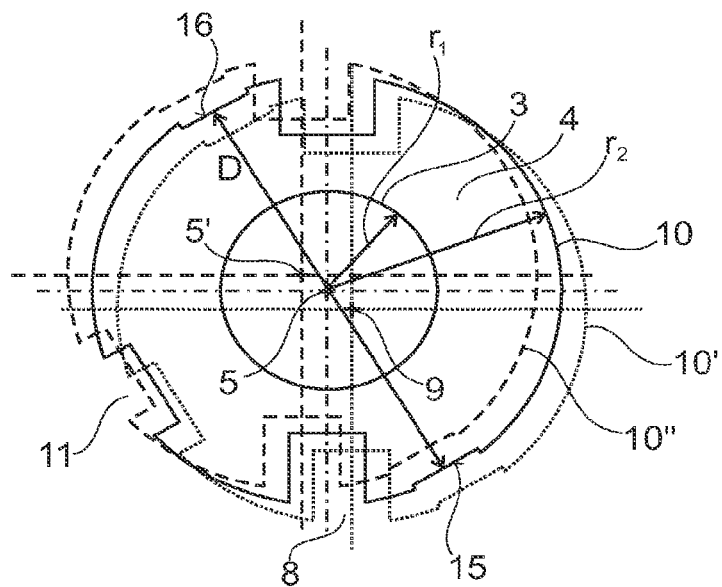
FIG. 7 is a diagram showing the geometrical situation to be allowed for in respect of the handle shown in FIG. 5.

The handle 1 is usually fabricated as a turned part, which means that the radius r1, shown in FIG. 7, of the shank 3 will possibly have comparatively coarse tolerances, whereas the radius r2 of the circumferential surface 10 disposed on the disk 4 is required to be very precise, preferably in a tolerance range of not more than 10 µm.

If the handle 1 to be provided with the structures should be eccentrically clamped in the chuck (not shown) of a machining device having the center of rotation 9, a change in the position of the circumferential surface 10 toward the circumferential surface 10', shown by the dotted lines, results when the handle 1 is rotated about the center of rotation 9 and this positional change has an adverse effect on precision.

It may be advantageous for this reason to establish a relationship between the center axis 5 of the handle 1 and the center of rotation 9 of the machining device (not shown). This is known to a sufficient extent from the measured values obtained with reference to FIGS. 5 and 6 from the prior art.

However, the structures of the invention are not necessarily produced by turning, but instead can be produced by milling or drilling, for which purpose the turned part subsequently forming the handle is removed from the lathe and clamped in a milling machine or a drilling machine. Of course, it is possible to leave the turned part in the lathe if the lathe is coupled to a milling machine or a drilling machine. Of significance here is the fact that the coordinate system of the milling or drilling machine is not always exactly adapted to the coordinate system of the lathe, which means that the absolute position of the turned part in the lathe differs from that in the milling or drilling machine, as shown by the dashed line 10" of the circumferential surface, of which the center of rotation 5' is offset from the manufacturing axis 5. The structure 17 or the structure 11 produced by the milling or drilling machine will therefore be produced relatively to the circumferential surface 10" and not to the circumferential surface 10. This error can be determined in that the structures 15, 16 are produced at a precisely known distance D from each other, the structures being formed such that they cover the tolerance range of the misalignment when machined in the milling or drilling machine. In the exemplary embodiment, the structures 15, 16 are in the form of depressions, the base of which always represents a reference surface, the position of which will be determined subsequently, for example by means of the tool for machining the blank corpus.

Figure 8:
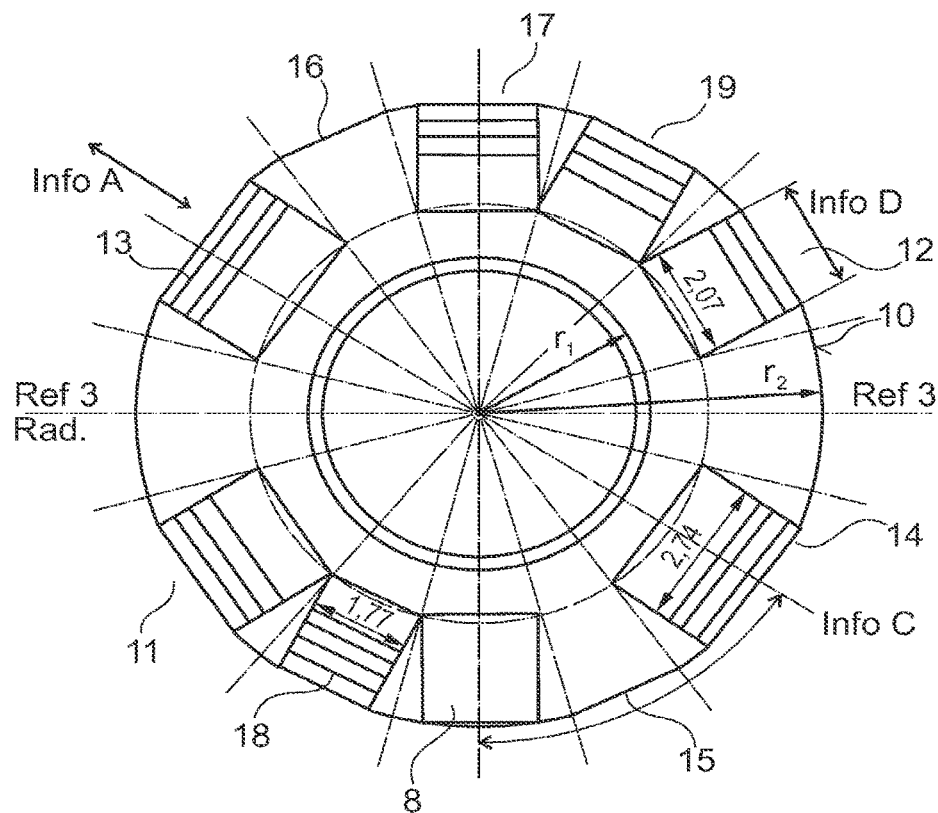
FIG. 8 shows, in detail, an embodiment of the structures on the handle shown in FIG. 5.

FIG. 8 shows an exemplary embodiment illustrating the design of the structures. The recess 8 required for positioning is in the form of a groove, as are the structures 11 to 14 and 17 to 19. The information supplied by the structure can be available from the depth of the groove, the width of the groove, the length of the groove, or the angular disposition of the groove. Thus, in structure 13, information A is provided by the depth and in structure 14, information C is provided by an angle g, the value of which is determined by the center between the two sidewalls of structure 14, and in the case of structure 12, information D is provided by the width of the structure. Each of these structures can provide additional information B (FIG. 9) from the length, and/or additional information A from the depth, of the structure.

The grooves of the structures 8, 11 to 14, 17 to 19 have, for example, parallel sidewalls and a base of the groove that is at right angles thereto.

All the structures are located at a defined angle relative to the position-setting groove 8, but it is possible to provide a positioning aid on the shank 3 instead of the position-setting groove 8 on the disk. It is essential in this respect that the handle 1 be held in a precisely predetermined angular position in the machining device.

The two reference surfaces of the structures 15, 16 each represent a surface that is approximately perpendicular to the rotation axis, the distance between said surfaces being known. By virtue of the fact that the position of these structures 15, 16 is detected, for example, with the aid of a contacting operation, the center axis of the handle 1 can be determined with micron precision from the standard contacting operation in combination with the data hitherto acquired concerning the center of rotation 9.

The structures of the coding means in the case of the recesses 11 to 14 and 17 to 19 illustrated, and the reference surfaces of the structures 15, 16 can be produced with the aid of the same tool in the milling or drilling machine as the one used for producing the groove 8 for setting the position of the handle 1. This makes it possible to precisely assign height information without requiring excessively high fabrication precision of the recesses relative to the circumferential surface 10 of the handle 1.

In the case of sufficiently precise manufacture, the two structures 15, 16 can be designed to provide information instead of acting as reference means in that the position of the reference surfaces is detected and a predefined meaning is derived from said position.

The depressions are dimensioned such that the tool of the machining device, usually a grinder or a milling cutter for the blank corpus, always finds space within the recess in spite of any positioning inaccuracies and tolerances present in the machining device. As an example, the width of the structures 18, 12, 14 is specified as 1.77 mm, 2.07 mm and 2.74 mm respectively for a tool diameter of 1.5 mm.

The depth of the recesses relative to the circumferential surface 10 or to the structures 15, 16 of the handle 1 represent the assigned analog information. These depths are in a range of from 0.5 to 2.5 mm relative to the circumferential surface 10.

In their longitudinal direction, that is, in the direction of the longitudinal axis 5, the structures can terminate before reaching the joining surface between the handle 1 and the blank corpus 2 in order to achieve a continuous adhesive surface on the upper side of the disk 4.

Figure 9:
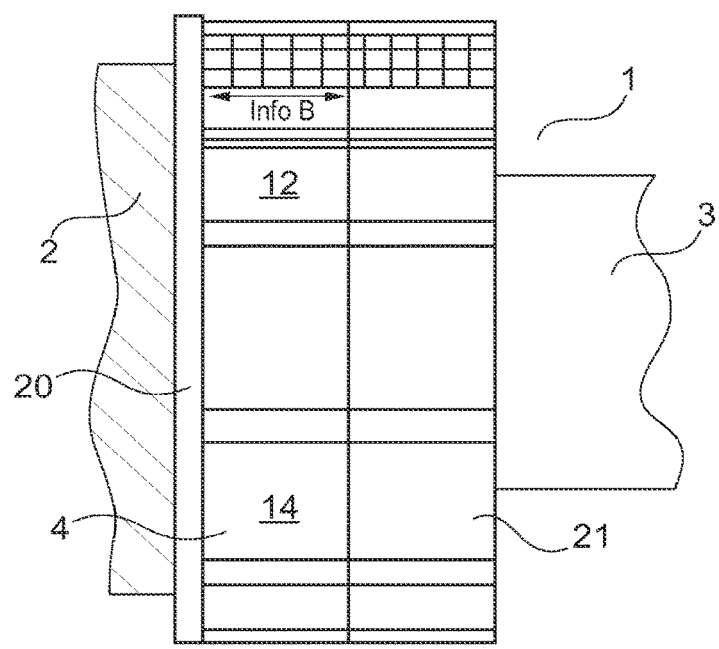
FIG. 9 shows a handle comprising a slidable ring provided with structures.

In addition to the shank 3 and the disk 4, the handle 1 in FIG. 9 comprises a partition plate 20 which prevents adhesive from entering the structures 12, 14 mounted on the disk 4 during the joining process with the blank corpus 2, which is only indicated in the figure.

In addition to or in place of the structures 12, 14 on the disk 4, a ring 21 can be provided which is pushed over the shank 3 toward the disk 4 and is optionally connected to the latter. Additional, or the same, structures 11-19 may be included in the ring 21 in order to provide further, or the same, information.

Alternatively, only the partition plate 20 is connected to the shank 3, and the disk 4 supporting the structures is only in the form of a slidable ring.

Figure 10:
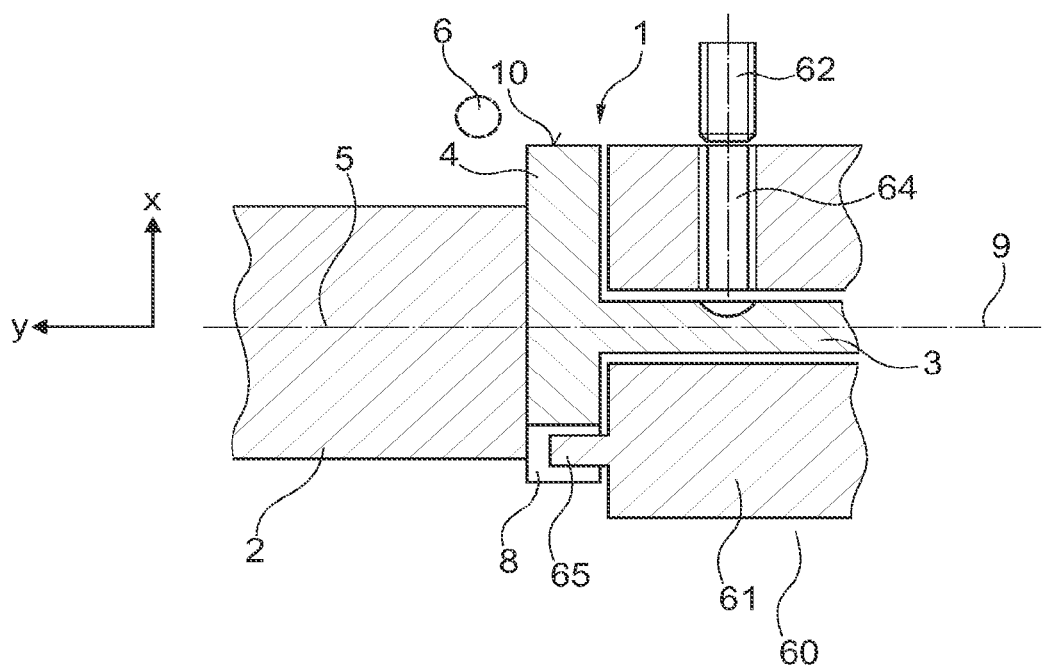
FIG. 10 shows a handle clamped in a machining device.

FIG. 10 shows a section of the blank mounted in a workpiece holder 60 of a machining device. The handle 1 is mounted by means of its shank 3 in a chuck 61 of the workpiece holder 60 with the aid of a set screw 62 which can be screwed into a corresponding threaded bore 64 in the chuck 61 and locked in place on the shank 3. In the ideal case, the longitudinal axis 5 of the handle 1 coincides with the center of rotation 9 of the workpiece holder 60.

By means of the depression 8 in the disk 4 connected to the shank 3, the handle 1 partially engages a projection 65 present on the chuck 61, so as to define the angular position of the handle 1 on the chuck relative to the center of rotation 9. An assignment of the angular position between the disk 4 and the chuck 61 can, as in the prior art, alternatively be realized at a different location between the disk 4 and the chuck 61 by the employment of unambiguous geometrical matching. The angular position of the chuck 61 of the workpiece holder 60 relative to the center of rotation 9 is known to the machining device so that there is an unambiguous starting position.

The blank corpus 2 (illustrated only in part) is mounted on the disk 4 and extends in the y-direction along the center of rotation 9. A tool 6, by means of which different contacting operations can be carried out on the handle, more precisely on the circumferential surface 10 of the disk 4, or on the blank corpus 2, is indicated beyond the plane of the cross-section.

It is evident from FIGS. 11 to 16 that the structures can alternatively be mounted on the blank corpus itself. This is explained below.

Due to the large number of different blank corpuses having various dimensions and material characteristics, it may be convenient to provide structures having information concerning the blank corpus alternatively or exclusively on the blank corpus itself. The information can be distributed over the handle and the blank corpus in any desired manner. For example, a property such as the width or the height of the blank corpus can be assigned to a structure existing at a defined position.

Also in the case of structures provided on the blank corpus, it is of paramount importance that at least the approximate positions of the structures carrying information be known to the machining device. Proceeding from a defined position as the starting point, this information should be acquired as rapidly as possible in order to accelerate the overall production process. For this purpose, it is also essential that the angular position of the handle and/or of the blank corpus supporting the structures relative to the workpiece holder be known or is at least determinable.

Figure 11:
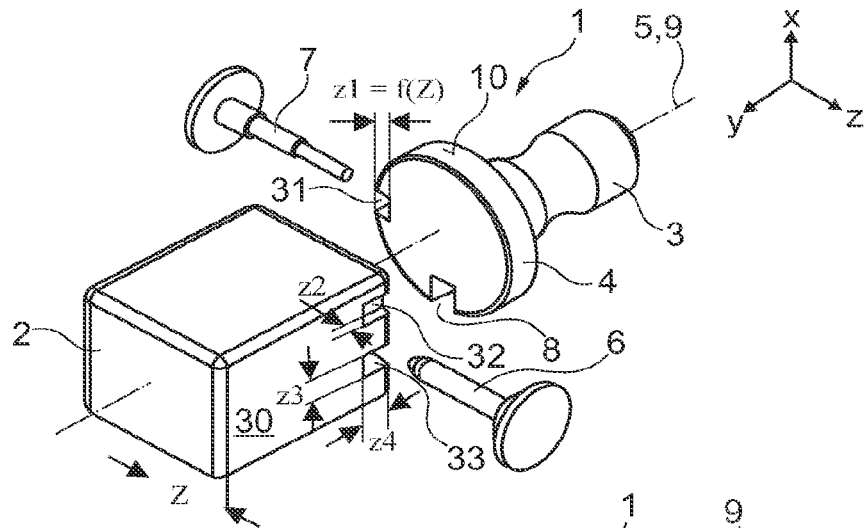
FIG. 11 shows a blank comprising a structure on the handle and comprising additional structures on the blank corpus.

In FIG. 11, the structures 31 to 33 carrying information are located partly on the handle 1 and partly on a lateral surface 30 of the blank corpus 2, which lateral surface 30 forms the reference surface. The first starting position for checking the blank for structures carrying information is the known circumference of the handle 1, the precision of the circumferential surface 10 being within a tolerance range of 10 μm.

For determining the second starting position, the machining device checks, by causing the tool 7 to slowly approach the circumferential surface 10 of the handle 1 of the blank, whether structures carrying information concerning the blank corpus 2 are present at one or more predefined positions of the handle 1. This process involving the careful approach of the tool is referred to as "contact scanning" or as a "contacting operation".

In the case illustrated, a structure formed as a recess 31 is provided only in one position on the circumferential surface 10 of the handle 1. From the depth of the recess 31 relative to the circumferential surface 10 of the handle, a value z1 is derived which, in this case, contains information concerning the position of a reference surface 30 possibly carrying additional information. This information can be the dimension of the blank corpus in a certain direction, which signifies, for example, the distance Z of the reference surface 30 from the rotation axis 9 of the handle 1 mounted in the workpiece holder as analog information.

The blank corpus is mounted precisely on the handle within predetermined tolerances relative to the longitudinal axis 5 of the handle. Furthermore, the tolerance of the deviation of the rotation axis 9 of the workpiece holder and of the longitudinal axis 5 of the handle is known. These tolerances are allowed for when prepositioning the tool on the reference surface 30.

The precision of the analog information provided by the structure 31 lies in the range of 10 µm, a factor being used, if required, in order to obtain the actual dimensions in millimeters. Thus, a dimension of 12 mm can correspond to a value of 1.2 mm, as determined by contact scanning when the factor stored in the machining device is 10.

Based on this information, the tool 6, whose position relative to the handle 1 is known, is initially prepositioned for an additional contacting operation on the corresponding lateral surface of the blank corpus 2 acting as a reference surface 30, and the exact position of this lateral surface of the blank corpus acting as reference surface 30 in the z direction is then determined by contact scanning.

After determining this accurately detected z position on the lateral surface acting as reference surface 30, this position can be taken as a second starting position for querying further structures 32, 33 located in this lateral surface and carrying certain information.

The x,y dimensions of the structures 32, 33 can be at least sufficiently large for the tool to reliably enter the structure 32, 33 even when the blank corpus 2, which has a coarse maximum tolerance in the x direction compared with the manufacturing precision, is eccentrically mounted. The y position of the handle itself is also known within a tolerance range of the order of magnitude of the manufacturing precision. When attaching the blank corpus 2 to the handle by means of an adhesive layer, a maximum deviation, which can likewise lie within a coarse tolerance range, will occur due to the adhesive layer between the blank corpus 2 and the handle in the y direction.

In the case of a diameter of a machining tool of 1.6 mm, an x,y dimensions of more than 2.0 mm×2.0 mm will be suitable for the structure 32, 33 in order to ensure that the tool can detect the structures reliably. For this purpose, the dimensions of the structures in the x, y direction should be at least 1.1 times the diameter of the largest machining tool used for the scanning procedure.

The position of the structures 32, 33 attached to the lateral surface 30 of the blank corpus 2 in the form of recesses extending in the x and y directions, that is, from top to bottom and from left to right in the plane of the drawing, are known to the machining device. For determining the depth in the z direction, the lateral surface 30 can be used as the reference surface.

The inside width of a recess is at least sufficiently large for the tool 6, 7 to find space between the sidewalls delimiting the recess. These recesses forming the additional structures 32, 33 carry information for the values z2 to z4 which reflect, for example, the dimensions of the blank corpus in the x and y directions and control information. For this purpose, a recess can have a dimension z3 in the x direction or a dimension z4 in the y direction, which dimensions can be detected with the aid of a contacting operation.

The information of the values z2 to z4 can also refer to the position of additional structures (not shown in the drawing) having values (zN-zM) for further information.

Prepositioning of the tool for the additional contacting operations in the region of these structures 32, 33 is carried out based on the knowledge of the predetermined average positions of these structures and the previously determined position of the blank corpus or the lateral surface 30 carrying the structures in the z direction.

By contact scanning, say, the recess of the lower structure 33 in the x direction, that is upwardly and downwardly, to sense the sidewalls of the recess, the value z3 can be acquired, assuming that the tool diameter is likewise known. The value z3 then indicates, for example, the dimension of the blank corpus in the x direction.

By contact scanning, say, the recess of the lower structure 33 in the y direction, that is from left to right, to sense the sidewalls of the recess, delimited in this case at one end by the surface of the handle 1, the value z4 can be acquired, the tool diameter again being known. The value z4 then indicates, for example, the dimension of the blank corpus in the y direction.

By contact scanning, say, the recess of the upper structure 32 in the z direction, the value z2 can be acquired, the position of the lateral surface 30 of the blank corpus being known, so that z2 represents the difference between the base of the recess and the lateral surface 30, that is, the depth of the recess. The value z2 is then serves, for example, as control information on the values z1, z3 and z4.

Figure 12:
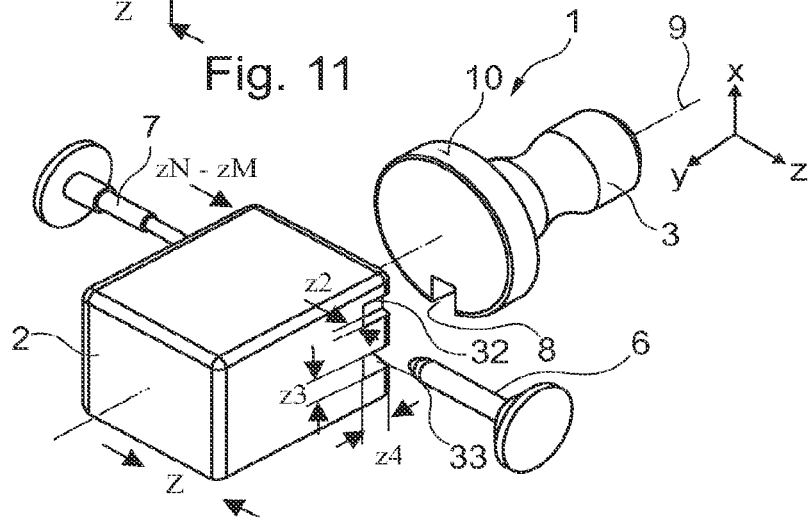
FIG. 12 shows a blank with no structures on the handle and comprising structures on the blank corpus only.

In FIG. 12, all structures 32, 33 carrying information are provided only on the blank corpus 2. The first starting position is again the known circumferential surface 10 of the handle 1 clamped in the machining device and positioned by means of the recess 8 in terms of its angular position relative to the rotation axis 9 of the machining device. At none of the at least one predefined position on the circumferential surface 10 of the handle does the machining device find a structure carrying information during at least one contacting operation of the tool 7 on the circumferential surface of the handle. In this case, the tool 6, 7 is prepositioned on the blank corpus 2 at positions corresponding to a predetermined dimension of the blank corpus in the z direction, e.g. the largest possible blank corpus of a plurality of variably large blank corpuses, and the precise position of the blank corpus, i.e. its lateral surface 30, in the z direction is detected by carrying out a contacting operation on the lateral surface 30.

This is of advantage, for example, when a large number of blank corpuses of different sizes have the same, in particular the largest possible, dimension in the z direction. In this case, a recess in the handle relating to this dimension can be dispensed with entirely, which results in a reduction in the cost and variety of handles and a reduction in the time taken for the tool to approach the blank, since this contacting operation is omitted.

The subsequent starting position is the determined z position of the reference surface 30 of the blank corpus, which reference surface incorporates the structures 32, 33, and the other values z2 to z4 are detected by carrying out additional contacting operations on the structures 32, 33 on the reference surface 30 as described above.

The structures in FIGS. 11, 12 can be produced by means of additional machining operations or, when the corpus is made by a pressing or casting process, the geometry of the die can produce such structures without additional machining operations.

Figure 13A:
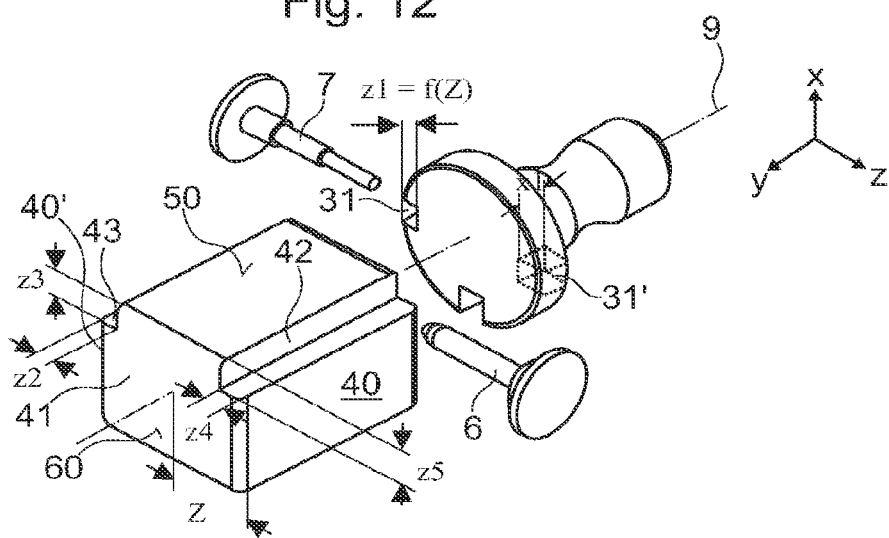
FIGS. 13A-C illustrate a blank comprising two structures on the handle and additional continuous structures on the blank corpus, FIGS. 14A,B show a blank comprising structures on the blank corpus, which structures relate to position and angle, FIGS. 15 A,B show a blank comprising a structure with a double bevel, FIGS. 16 A,B show a blank comprising an outwardly oriented structure.

In the case of a blank corpus 41, as shown in FIG. 13A and produced in an extrusion process, the structures can be in the form of recesses extending over the entire length of the blank corpus and produced without additional machining operations.

Figure 13B:
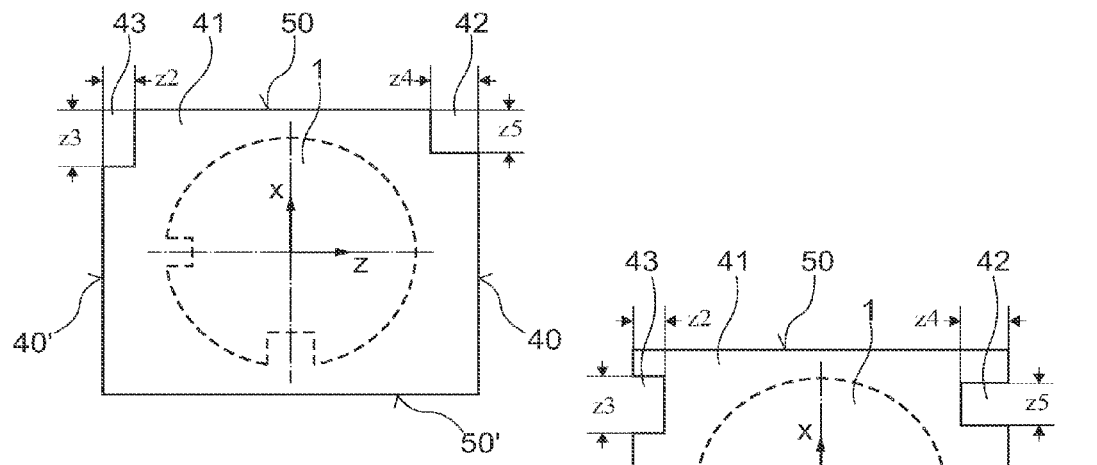
Figure 13C:
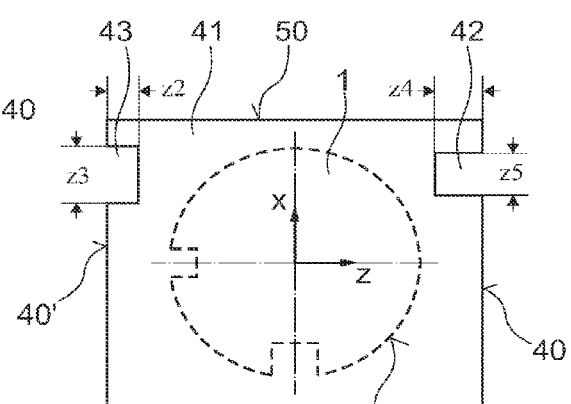

The structures 42, 43 having the values z2 to z5 can be formed, as shown in FIGS. 13A, 13B, as recesses at the edges or also as grooves, as shown in FIG. 13C, in the lateral surface 40, 40' of the blank corpus 41. FIGS. 13B, 13C are shown as top views of the blank corpus 41 as viewed in the y direction, for the sake of clarity.

The first starting position is again the known circumferential surface 10 of the handle. Information concerning the value z1 is acquired from the depth of the structure 31 formed as a recess in the circumferential surface of the handle, and it represents the position of the lateral surface 40 of the blank corpus 41 relative to the rotation axis 9 of the tool holder. This information is used for optimized prepositioning of, say, the tool 7 shown on the left side of the drawing for carrying out the contacting operation on the hidden lateral surface 40' of the blank corpus 41 for the purpose of detecting the precise position of said lateral surface 40' to be used as the reference surface for acquisition of the value z2 from the structure 43, for example.

For prepositioning the tool 7 on the structure 43 in the x direction for acquisition of the value z3, a second structure 31' can be incorporated in the circumferential surface of the handle, for example, opposite the recess forming the structure 31. While one tool, in this case tool 7 on the left side of the drawing, acquires the value z1 of the recess 31, the other tool, in this case tool 6 on the right side of the drawing, can simultaneously acquire the value x1 of the recess 31'.

For acquisition of the value z3, the tool 7 then approaches the lateral surface 50 starting from the preposition, in order to detect the precise position of this lateral surface 50 in the x direction. After detecting the precise position of the lateral surface 50, the tool 7 approaches the structure 43 in the x direction. The value z3 is then acquired from the difference between the position of the reference surface 50 and the position of the structure in the x direction, that is, a surface of the shoulder of the structure 43, which surface is located in the x, y plane. The same applies to the value z5, in which case the tool 6 is used for the contacting operation.

The additional values z4, z5 are acquired as described above.

The structures can also be formed as slanting surfaces, for example, as bevels, the position of the slanting surface on the blank corpus 41 representing a first piece of information, and the angle of the slanting surface representing a second piece of information. This is shown in FIGS. 14A-16B.

Figure 14A:
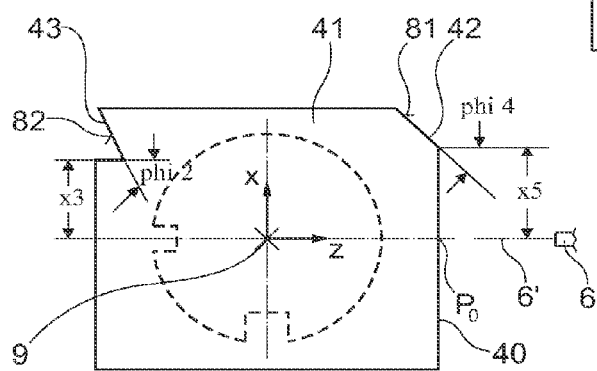

A position $P_0$, shown in FIG. 14A, having the x, y coordinates x0 and z40 is given during the contacting operation on the surface 40 by the tool 6 moving along the tool axis 6' extending through the rotation axis 9 of the workpiece holder and thus also along the z axis.

The structure 42 located at a distance x5 from the z axis in FIG. 14A is in the form of a bevel on the edge of the blank corpus and thus cuts off a portion from the blank corpus 41. On the other hand, the structure 43 located at a distance x3 cuts out a portion of the blank corpus 41. Common to both structures are slanting surfaces extending along the y direction at angles of phi 4 and phi 2 respectively to the z axis.

Figure 14B:
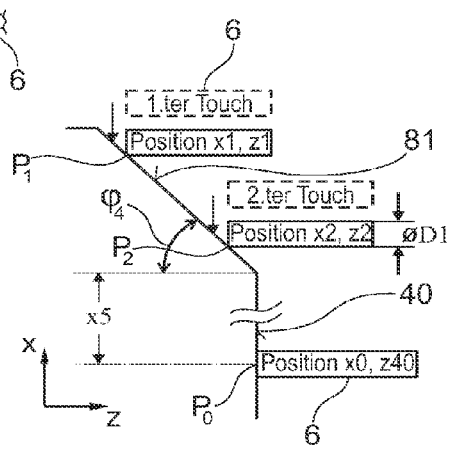

FIG. 14B shows the manner in which the position and the angle of the slanting surface 81 of the structure 42 are detected.

Starting from the position $P_0$ with the coordinates x0, z40, a value x1 can be acquired in the x direction at a first position $P_1$ having a predetermined value z1 by a first contacting operation of the tool 6 on the slanting surface 81 against the x direction. A value x2 can be acquired in the x direction at a second position $P_2$ having a predetermined value z2 in a second contacting operation. The z values z1 and z2 of the positions $P_1$, $P_2$ are thus specified based on the z value of the position $P_0$ z40, e.g. z1=z40+3 mm and z2=z40+1 mm. The positions x1 and x2 are given by the contacting operation of the bevel in the x direction.

Alternatively, the positions $P_1$, $P_2$ can be specified by means of the values x1 and x2, based on x0. The values z1 and z2 are then given by the contacting operation of the surface 81 carried out by the tool 6 moving in the z direction.

The angle phi 4 is calculated as follows:

$$\text{phi4}=\arctan\left[(x1-x2)/(z2-z1)\right]$$

The value x5 is calculated as follows for a known value of the tool diameter D1:

$$x5=(x2-\tfrac{1}{2}*D1)-[(z40-z2)*\tan(\text{phi4})]+x0$$

The values phi 2 and x3 shown in FIG. 14A are acquired in a similar manner.

For production reasons, it may be advantageous to design a structure such as the structure 43 shown in FIG. 14A as a double bevel comprising two convergent slanting surfaces, as shown in FIGS. 15A, B. A first advantage consists in a preferably obtuse angle in the case of a blank corpus of ceramic material and a second advantage is an improved mold release in the case of compression molded parts.

Values z1, z2 and z3 can be acquired in the case of a known value x6 as the measure of the position of the double bevel in the blank corpus 41, which measure corresponds to the largest distance from the surface 40, and in the case of a prepositioning for contacting operation depending on x6 at the positions $P_1$ to $P_3$ having the values x1, x2, x3. Information concerning x5 and phi 4 is calculated as follows, for a known value of the tool diameter D1:

$$\text{phi4}=\arctan\left[(x1-x2)/(z2-z1)\right]$$

$$x5=(x2-\tfrac{1}{2}*D1)-[(z40-z2)*\tan(\text{phi4})]+x0$$

In the case of a structure comprising an asymmetrically shaped double bevel having two slanting surfaces 81, 82 inclined at different angles phi 4, phi 5 to the z axis, an additional piece of information stored in the form of an angle phi 5 can be determined in an additional contacting operation at the position $P_3$. Information concerning x5 and phi 4 and phi 5 is calculated as follows, for a known value of the tool diameter D1:

$$\text{phi4}=\arctan\left[(x1-x2)/(z2-z1)\right]$$

$$x5=(x2-\tfrac{1}{2}*D1)-[(z40-z2)*\tan(\text{phi4})]+x0$$

$$\text{phi5}=\arctan\left[((x3+\tfrac{1}{2}*D1)-x6)/((x6-x5)/\tan(\textit{phi4}))-(z40-z3))\right]$$

As shown in FIG. 16A, a structure 52, 53, which projects from a blank corpus without no information concerning the blank corpus 51, can also be provided. The values for x3, x5 and phi 2, phi 4 are acquired similarly to FIG. 13B by the approach of the tool toward the slanting surfaces 81, 82. FIG. 16B shows that the structures 52, 53 need not extend over the entire length of the blank corpus.

These structures can also be in the form of symmetrical or asymmetrical double bevels.

The contacted positions in the y direction can vary depending on the process used for forming the structures as grooves or slanting surfaces, i.e. the contacting operation can be carried out at different distances from the handle for optimizing the distances traveled. After a tool fracture and a restart of the contacting operation, it is possible, for example, to allow for the unmachined residual length of the blank corpus in this case when carrying out prepositioning in the y direction.

For production reasons and for the formation of a blank corpus in a manner that is suitable for ceramic materials, it may be advantageous to make all of the edges of the blank corpus beveled or rounded as disclosed in the prior art.

However, as a general rule, these structures need not extend over the entire length of the blank corpus whether it be extruded or pressed into a mold or subjected to additional machining operations. Theoretically, the structures can be full length of partial length on any of the four lateral surfaces 40,40',50, 50' or either of the two end faces 60, i.e. that end face near the handle which is not denoted by any reference sign and the exposed end face 60 of the blank corpus.

The formation of the recess over the entire length of the blank corpus is also possible in the case of a compression-molded blank corpus. The compression mold used for production is fabricated by the removal of material from the interior of the mold such that the ceramic material does not completely fill the volume of a cuboid in certain regions. The compression mold can also be formed by removing material from the interior of the compression mold such that the ceramic material will protrude from the volume of a cuboid in certain regions.

A small-area recess such as the one shown in FIGS. 11 and 12 can lead to inhomogeneity and internal stresses in the case of certain materials. A structure distributed uniformly over the blank corpus such as the one shown in FIGS. 13 and 14 can reduce this effect.

Structures, in which the information is acquired from the depth of the recesses relative to the detected position of a reference surface, i.e. structures of which the depth of the recess is detected, are particularly suitable in all embodiments. The advantage over structures in the form of projections is that prepositioning can be carried out at the level of the reference surface.

Instead of using depressions having evaluated dimensions such as those denoted by reference signs $z2$, $z3$, $z4$ in FIG. 11 and are detected in terms of their depth $z2$ and distances $z3$ and $z4$, it is possible to use other appropriate designs, for example an appropriately large cylindrical recess of the same depth $z2$ and having a diameter $z3$ or $z4$ as a depression for the purposes of the invention.

Particularly when the information of a structure is available only in the z direction, the shape of this structure is arbitrary in the x and y directions provided the tool can scan the depth information in the z direction without hindrance.

All combinations of the provision of structures carrying information on the handle and the provision of structures carrying information on the blank corpus at positions known to the machining device are possible.

Four items of information can then be distributed, for example, as follows:
One depression of defined depth located on the handle and three depressions of defined depth located on the blank corpus, or:
Four depressions of defined depth located on the blank corpus.

For comprehension of the advantages of the invention it is important to realize that in the prior art, apart from the contacting operations carried out on the handle 1 of the blank, it may also be necessary to carry out a contacting operation on the blank corpus 2 itself in order to determine the dimensions of the blank corpus. The contacting operation on the blank corpus 2 itself can now be carried out in a shorter period of time due to the optimized prepositioning of the machining tool used for said contacting operation.

A further important advantage resulting from the knowledge of the dimensions of the blank corpus 2 is that, due to the detected dimensions, the paths traveled by the tool when machining the blank corpus can be adapted to suit these dimensions. For example, if the shaped body to be produced by the removal of material is disposed in the blank corpus 2 in such a way that the tool cannot produce the entire shape intended for it on account of having reached the maximum advance position, a complete machining operation of the blank corpus can be carried out if the blank corpus 2 is rotated through 90° for final machining. This machining step is referred to as a corrective procedure. In order to prevent any unmachined residual material of the blank corpus 2 from blocking access to the shaped body already machined in part, not only is the material surrounding the shaped body removed but also that material of the blank corpus 2 which is situated between the shaped body and the edges of the blank corpus is removed.

Since the position of the edge of the blank corpus 2 in this machining direction has hitherto been unknown, the maximum dimensions have always been the criterion for the starting point and the path to be traveled by the tool has been taken to start from this maximum dimension of a blank corpus. Based on the knowledge of the actual dimension of the blank in this direction, the tool path can now be reduced to said actual dimension, which can result in a saving of machining time of up to 10%.

The size of the blank to be machined is restricted to the limited size of the machining chamber for the tools.

After a successful contacting operation or after machining the blank corpus 2 using a tool, the control information or a structure can be changed for further machining of the blank corpus or additional information can be included, in order to prevent improper reuse of the handle 1 or to store information concerning, for example, the material removed so far from a partially machined blank corpus 2.

The contacting operation can be adapted to react either to the rotational speed of the tool or to the force applied to the machining tool or to both.

Instead of evaluating the structure with the aid of a contacting operation by a tool, the structure can be scanned by optical means provided in the machining device and adapted to scan the blank in the region of the structures after it has been inserted into the machining device but prior to machining. A machining device comprising a scanning device suitable for this purpose is disclosed in DE 199 50 780 A1. Particularly in the case of a point sensor, the sensor must also be advanced toward the structure, as a result of which adjustment positioning is necessary.

The features and approaches described for individual exemplary embodiments only can, as a rule, also be applied to the other exemplary embodiments.

The invention claimed is:
1. A method for producing a dental shaped body from a blank having a corpus of tooth restoration material by a tool adapted to remove said material, wherein, to detect a position of said corpus inserted in a machining device, contact scanning is performed on said blank by said tool, the method including steps of:

providing a machining tool in a first position;

detecting at least one geometric structure on said blank, the at least one geometric structure defines information that corresponds to at least one relevant dimension of said blank corpus; and using the information that corresponds to said at least one relevant dimension of said blank corpus to preposition said machining tool to a second position at or close to a first reference surface or a first reference structure for a contacting operation;

determining a position of the first reference surface or first reference structure by contact scanning from said second position; and using the determined position as a starting position to detect one or more other geometric structures and/or to perform one or more other contact scanning such that contacting times of the tool during contact scanning and/or machining times of the tool during machining are reduced.

2. The method as defined in claim 1, wherein a size of said blank corpus is detected in the detecting, and further comprising reading a coding device that includes at least one geometrical structure, a size of said at least one geometrical structure representing, according to an analog function, at least one dimension of said blank corpus.

3. The method as defined in claim 2, further comprising reading a further structure that provides information regarding at least two other further structures.

4. The method as defined in claim 3, wherein, upon reading of false information, machining is stopped.

5. The method as defined in claim 2, further comprising converting an acquired value to a linear dimension using a conversion function that is independent of said blank.

6. The method as defined in claim 2, wherein said coding device detects a size of said blank corpus, and is scanned by said tool by way of said contacting operation.

7. The method as defined in claim 1, wherein said geometric structure comprising at least one surface, deviates in position, dimension or nature of said surface from that of a predefined reference surface, which deviation corresponds to information concerning the blank corpus.

8. The method as defined in claim 7, wherein the predefined reference surface is a circumferential surface of the corpus handle.

9. The method as defined in claim 7, wherein the predefined reference surface is a lateral surface of the blank corpus.

10. The method as defined in claim 1, wherein a contacting path is delimited according to said at least one dimension of said blank corpus detected in said detecting.

11. The method as defined in claim 1, wherein, following said contacting operation and/or following machining of said blank corpus, a structure is modified and/or a further structure is produced by said tool.

12. The method as defined in claim 1, further comprising detecting at least one dimension of said blank corpus by said contacting operation on geometric structure located on said corpus.

13. The method as defined in claim 1, further comprising detecting a position of a structure located on said corpus by scanning a structure located on a handle of said blank.

14. The method as defined in claim 1, further comprising detecting a position of a structure located on said corpus by scanning a structure located on said corpus.

* * * * *